(12) United States Patent
Kadobayashi

(10) Patent No.: US 8,002,549 B2
(45) Date of Patent: Aug. 23, 2011

(54) SET OF ARTIFICIAL TEETH WITH NO ABUTMENT AT HIGHEST CONTOURS

(75) Inventor: Yusei Kadobayashi, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 0 days.

(21) Appl. No.: 12/707,090

(22) Filed: Feb. 17, 2010

(65) Prior Publication Data

US 2011/0039230 A1 Feb. 17, 2011

(30) Foreign Application Priority Data

Aug. 12, 2009 (JP) .................................. 2009-187207

(51) Int. Cl.
*A61C 13/10* (2006.01)
(52) U.S. Cl. .......................... 433/196; 433/171; 433/197
(58) Field of Classification Search .......... 433/167–172, 433/182–183, 191, 197, 196; 264/16–17
See application file for complete search history.

(56) References Cited

U.S. PATENT DOCUMENTS

| | | | |
|---|---|---|---|
| 3,710,446 A * | 1/1973 | Poveromo | 433/182 |
| 4,556,389 A * | 12/1985 | Ueno et al. | 433/206 |
| 4,740,160 A * | 4/1988 | Hruska | 433/219 |
| 5,486,110 A * | 1/1996 | Wilson et al. | 433/177 |
| 7,040,885 B2 * | 5/2006 | Price et al. | 425/176 |

FOREIGN PATENT DOCUMENTS

JP 9-220242 8/1997

OTHER PUBLICATIONS

Kogure, "Machine Translation of JP 09-220242", Accessed Apr. 23, 2010 from JPO website.*

* cited by examiner

*Primary Examiner* — Cris L Rodriguez
*Assistant Examiner* — Edward Moran
(74) *Attorney, Agent, or Firm* — Wenderoth, Lind & Ponack, L.L.P.

(57) ABSTRACT

The present invention is to provide a set of easily arranged artificial teeth in which shapes of abutment surfaces of adjacent artificial teeth are not varied. In the set of artificial teeth, at least two artificial teeth adjacent to each other in a mesial-distal direction respectively have highest contours, one of the highest contours on the adjacent sides is positioned on an occlusal surface side and a buccal surface side relative to the other, and the artificial teeth are abutted with each other at abutment positions between the highest contours of both the artificial teeth in the occlusal direction and the buccolingual direction. Parting lines of molds for forming the artificial teeth respectively pass through the highest contours.

8 Claims, 3 Drawing Sheets

SET OF ARTIFICIAL TEETH WITH NO ABUTMENT AT HIGHEST CONTOURS

BACKGROUND OF THE INVENTION

1. Field of the Invention

The present invention relates to a set of artificial teeth for producing a dental prosthetic appliance.

2. Description of the Related Art

There is a need for advanced technique and experience for arrangement of artificial teeth at the time of producing a dental prosthetic appliance (plate dentures).

Although an artificial tooth is formed by a mold in general, it is not suitable to provide a parting line of the mold on a buccal surface and an occlusal surface for functional and aesthetic reasons. Therefore, as described in Japanese Unexamined Patent Publication No. 9-220242, the parting line of the mold is positioned on surfaces of the artificial tooth in a mesial-distal direction. For forming a shape for drawing the artificial tooth out from the mold, the parting line of the mold is provided so as to pass through the highest contours of the artificial tooth.

A burr is generated on the parting line on the surfaces of the artificial tooth formed by the mold. Thus, when this burr is removed by grinding or the like, shapes of the surfaces of the artificial tooth in the mesial-distal direction, particularly shapes in the vicinity of the highest contours vary contrary to what was designed.

The artificial tooth is abutted with an artificial tooth adjacent in the mesial-distal direction at the vicinity of the highest contours. Thus, it is difficult to recognize a positional relationship between the artificial teeth having the highest contours of varied shapes due to the burr removal described above, so that arrangement of the artificial teeth at the time of producing the dental prosthetic appliance becomes a more difficult operation.

SUMMARY OF THE INVENTION

In view of the above-mentioned problems, an object of the present invention is to provide a set of easily arranged artificial teeth in which abutment surfaces of adjacent artificial teeth are not varied.

In order to achieve the above object, a set of artificial teeth according to the present invention includes a plurality of artificial teeth, in which at least two artificial teeth adjacent to each other in the mesial-distal direction respectively have highest contours being at different positions from each other on adjacent sides, and the artificial teeth are abutted with each other at abutment positions which are different from the highest contours.

With this configuration, the adjacent artificial teeth are abutted with each other at the positions which are not the highest contours. Thus, even when shapes of the highest contours are changed by burr removal or the like, shapes of abutment parts are not changed. Therefore, at the time of producing a dental prosthetic appliance, a technician can easily recognize relative positions of the adjacent artificial teeth and relatively easily arrange the artificial teeth.

Moreover, in the set of artificial teeth according to the present invention, the artificial teeth may be formed by molds divided by parting lines respectively having up-down parting parts orthogonal to a substantially occlusal direction, and inside-outside parting parts orthogonal to a substantially buccolingual direction, and the parting lines may respectively pass through highest contours of the artificial teeth.

With this configuration, the parting lines are not formed on buccal surfaces and occlusal surfaces of the artificial teeth, and the artificial teeth can be molded with using normal two-divided molds with which shapes for drawing the artificial teeth are ensured.

Moreover, in the set of artificial teeth according to the present invention, one of the artificial teeth adjacent to each other in the mesial-distal direction may have the highest contour on the adjacent side to the other artificial tooth, the highest contour being positioned on the occlusal surface side and on the buccal surface side relative to the highest contour on the adjacent side of the other.

With this configuration, the parting lines of the molds passing through the highest contours can be provided so as not to pass through the buccal surfaces and the occlusal surfaces of the artificial teeth but to go through parted positions between the adjacent artificial teeth. Therefore, regions on the surfaces opposing to the adjacent artificial teeth which are not ground for the burr removal are large. Thus, the adjacent artificial teeth are abutted with each other at these regions so as to obtain shapes with which the artificial teeth are easily arranged.

Although expressions such as the buccal side and the buccolingual direction which are only for molar teeth in a precise sense are used in the present invention, this does not intend to limit the present invention to the molar teeth. In a case where the present invention is applied to incisors and canines, the buccal side and the buccolingual direction should be recognized as a labial side and a labiolingual direction. The expression of the lingual side also does not indicate that the present invention is only applied to the artificial mandibular teeth. The expression should be recognized as a term also indicating the palatal side in the teeth in a maxillary arch.

Moreover, in the set of artificial teeth according to the present invention, the artificial teeth adjacent to each other in the mesial-distal direction may be abutted with each other at the abutment positions between the highest contours of both the artificial teeth in the occlusal direction and the buccolingual direction.

With this configuration, by setting the abutment positions between the highest contours, the artificial teeth can be abutted with each other at the abutment positions which are different from the highest contours without complicating shapes of the artificial teeth.

Further, in the set of artificial teeth according to the present invention, the artificial teeth adjacent to each other in the mesial-distal direction may be in surface contact with each other.

With this configuration, relative positions of the artificial teeth can be easily determined.

Further, in the set of artificial teeth according to the present invention, the artificial teeth abutted with each other at the abutment positions which are different from the highest contours may be molar teeth.

The configuration of the present invention is easily applied to the molar teeth having large size in the buccolingual direction.

Further, in the set of artificial teeth according to the present invention, the artificial teeth may be formed by covering at least buccal surfaces and occlusal surfaces of base materials with a hard coat, and the base material may be covered with the hard coat at the abutment position of one of the artificial teeth adjacent to each other in the mesial-distal direction, and the base material may be exposed at the abutment position of the other artificial tooth.

With this configuration, the positions and the directions of the artificial teeth can be confirmed based on existence of the hard coat.

According to the present invention, since the positions of the highest contours and the abutment positions of the adjacent artificial teeth are varied between the artificial teeth, the abutment positions of the artificial teeth are not scaled to change the shapes at the time of removing the burr in molding of the artificial teeth. Therefore, since the relative positions can be recognized by abutment of the artificial teeth, it is possible to easily produce the dental prosthetic appliance.

BRIEF DESCRIPTION OF THE DRAWINGS

These and other objects and features of the present invention will become apparent from the following description taken in conjunction with the preferred embodiments thereof with reference to the accompanying drawings, in which.

DESCRIPTION OF THE PREFERRED EMBODIMENTS

Figure 1:
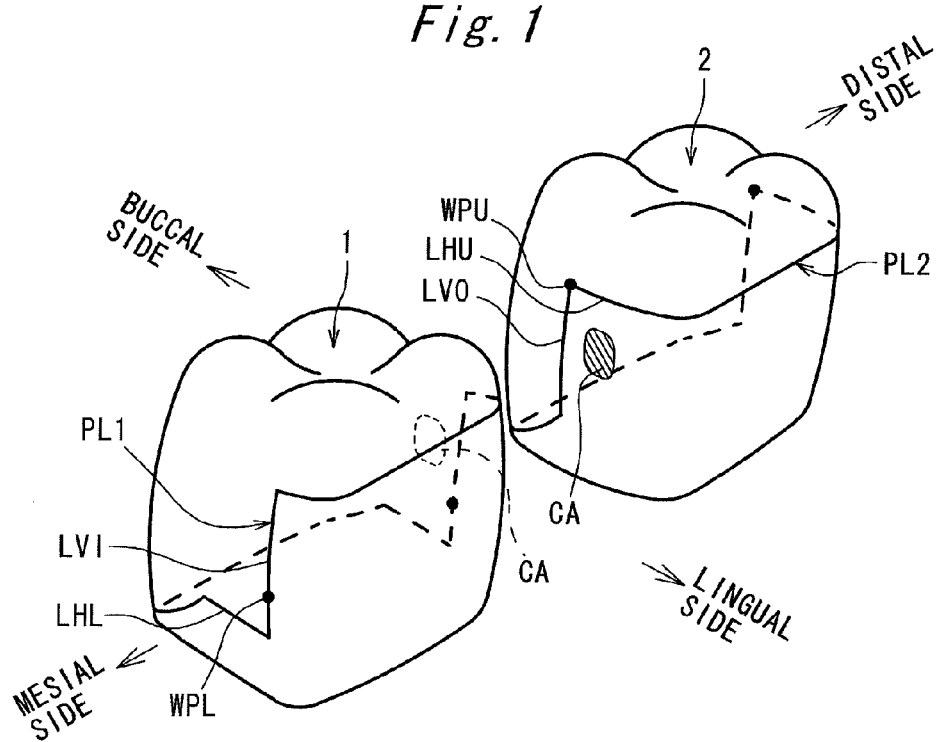
FIG. 1 is a perspective view of a set of artificial teeth according to a first embodiment of the present invention.
Figure 2:
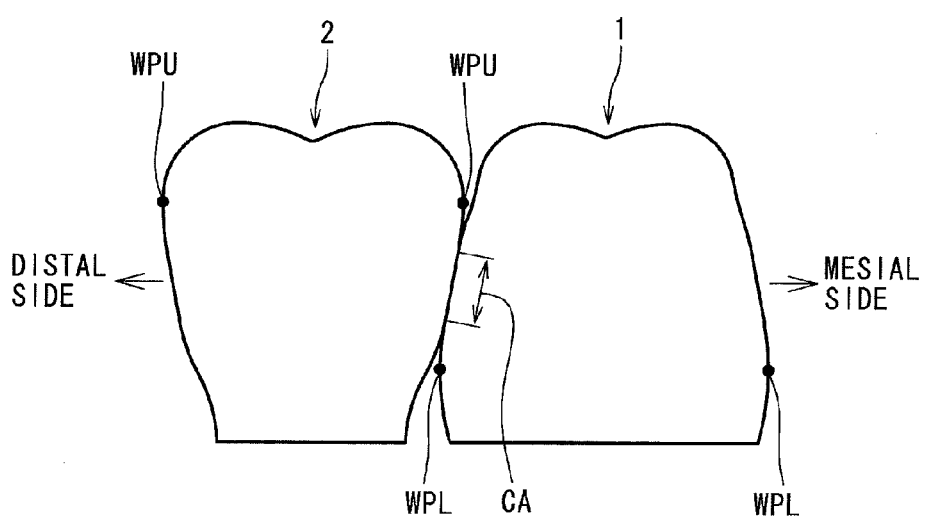
FIG. 2 is a front view of the artificial teeth in FIG. 1 seen from a buccal side.

FIGS. 1 and 2 show a set of artificial teeth according a first embodiment of the present invention. The set of artificial teeth according to the present embodiment includes an artificial mandibular first molar tooth 1 and an artificial mandibular second molar tooth 2.

The set of artificial teeth according to the present invention is preliminarily molded and provided, and is used by a dental technician for producing a dental prosthetic appliance, particularly plate dentures of full dentures and partial dentures. The set of artificial teeth according to the present invention includes at least two artificial teeth which are adjacent to each other, preferably includes four molar teeth (molar teeth and premolar teeth) arranged side by side, and may be provided as a set of all the artificial teeth in maxillary and mandibular arches including incisors and canines.

In the present embodiment, the artificial teeth 1 and 2 adjacent to each other in a mesial-distal direction respectively have the highest contours WPL and WPU which are the most protruding parts in the mesial-distal direction at different positions from each other in an occlusal direction and a buccolingual direction. The artificial teeth 1 and 2 are in surface contact with each other at abutment areas CA positioned between the highest contours WPL and WPU of both the artificial teeth.

In the present embodiment, the highest contours WPU of the artificial tooth 2 are positioned on the occlusal surface side and the buccal surface side relative to the highest contours WPL of the artificial tooth 1. The abutment areas CA are positioned between the highest contours WPL and WPU of the artificial teeth 1 and 2 in the occlusal direction and the buccolingual direction.

It should be noted that particularly in FIG. 2, shapes of the artificial teeth 1 and 2 are exaggerated for easy understanding.

The artificial tooth 1 and the artificial tooth 2 are respectively molded by two-divided molds. Parting lines PL1 and PL2 corresponding to division positions of the molds are shown in the figure. The parting lines PL1 and PL2 include up-down parting parts LHL and LHU substantially orthogonal to the occlusal direction, and inside-outside parting parts LVI and LVO substantially orthogonal to the buccolingual direction.

Figure 3:
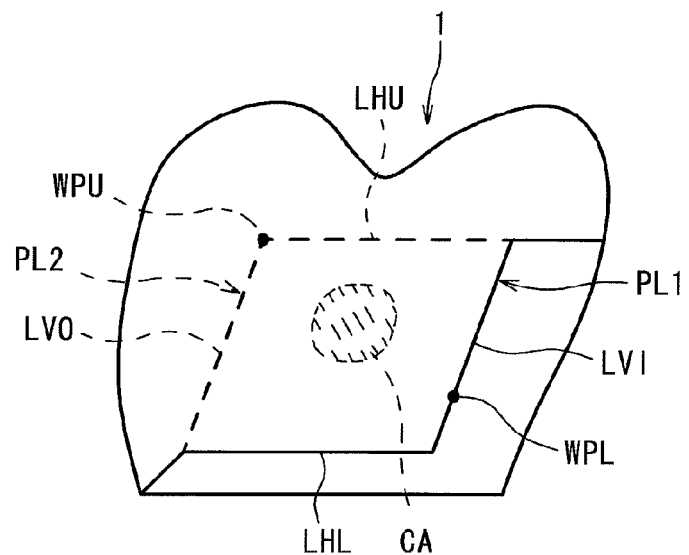
FIG. 3 is a side view of the artificial teeth in FIG. 1 seen from a mesial side.

The parting lines PL1 and PL2 are provided so as not to pass through buccal surfaces and occlusal surfaces but pass through the highest contours WPL and WPU of the artificial teeth 1 and 2, respectively. As shown in FIG. 3, when the artificial teeth 1 and 2 are seen from the mesial side, the abutment areas CA are surrounded by the up-down parting parts LHL and LHU and the inside-outside parting parts LVI and LVO of the artificial teeth 1 and 2.

In the present embodiment, the highest contours WPL and WPU on the adjacent sides of the artificial teeth 1 and 2 are disposed respectively differently in the occlusal direction and the buccolingual direction so that positions of the highest contours are shifted from each other when seen in the mesial-distal direction. Thus, the abutment areas CA at which the artificial tooth 1 and the artificial tooth 2 are abutted with each other can be provided at positions which are different from the highest contours WPL and WPU.

Therefore, even in a case where the two-divided molds are used for the artificial teeth 1 and 2 and the parting lines PL1 and PL2 are provided so as to pass through the highest contours WPL and WPU for forming shapes for drawing, the abutment areas CA are not scaled by an operation of removing burrs generated on the parting lines PL1 and PL2 of the artificial teeth 1 and 2.

In this manner, the artificial tooth 1 and the artificial tooth 2 have the abutment areas CA of fixed shapes. Thus, a relative-positional relationship between the artificial teeth is proper when the artificial tooth 1 and the artificial tooth 2 are abutted with each other at the abutment areas CA. Thereby, when a technician produces a dental prosthetic appliance, the artificial tooth 1 and the artificial tooth 2 can be easily arranged.

When the abutment areas CA of the artificial teeth 1 and 2 are formed on curved surfaces with which the shapes for drawing of the molds are not deteriorated such that the width of the artificial teeth 1 and 2 are monotonically increased toward the parting lines PL1 and PL2 in the direction in which the molds are removed, relative positions of the artificial teeth 1 and 2 are more easily recognized.

In the present embodiment, in order to sufficiently ensure the area of the abutment areas CA, preferably, the highest contours WPU on the occlusal surface side are positioned at one-third or less of height of the artificial teeth 1 and 2 in the occlusal direction (a distance from a most protruding cusp C to a bottom surface) from the occlusal surface, and the highest contours WPL on the bottom surface side are positioned at one-third or less of the height of the artificial teeth 1 and 2 in the occlusal direction (the distance from the most protruding cusp C to the bottom surface) from the bottom surface.

Further, the artificial teeth 1 and 2 are formed by providing hard coats made of enamel for example on faces of base materials made of dentin for example. The hard coats are only formed on the upper sides of the parting lines PL1 and PL2 so as to cover the entire occlusal and buccal surfaces. Thereby, the abutment area CA of the artificial tooth 1 is covered with the hard coat, while the base material is exposed at the abutment area CA of the artificial tooth 2.

In other words, the artificial tooth 1 and the artificial tooth 2 can be discriminated and the direction of the buccal side and the lingual side can be confirmed by disposition of the hard coats. While the hard coats are desirably colored with a color tone close to natural teeth, the base materials may be colored with a different tone from the hard coats so as to facilitate the discrimination.

In a case where the entire mesial surfaces and distal surfaces of the artificial teeth 1 and 2 are covered with the hard coats, layers including the hard coats and the base materials are formed in the burrs generated on the parting lines PL1 and PL2 at the time of compression molding by the molds, and the layers of the base materials emerge at the surface after scaling the burrs. Since the parting lines PL1 and PL2 can also be confirmed in this manner, the artificial tooth 1 and the artificial tooth 2 can be discriminated and the buccolingual direction of the artificial teeth 1 and 2 can be confirmed. The base materials of the artificial teeth 1 and 2 may have multi-layer structures themselves.

The hard coats on the occlusal surfaces of the artificial teeth 1 and 2 are thicker on the mesial side. Specifically, the hard coats of the artificial teeth 1 and 2 at the cusps on the mesial side are 1.03 to 3.5 times, preferably 1.1 to 1.2 times thicker than the hard coats at the cusps on the distal side.

This is to determine the life of the artificial teeth based on wear on the hard coats at the cusps on the distal side and maintain a mastication function by the cusps on the mesial side until the artificial teeth are prepared for replacement. Moreover, the thickness of the hard coats also provides an effect of easily discriminating the mesial-distal direction of the artificial teeth 1 and 2.

At the time of producing the molds of the artificial teeth 1 and 2, mold cavities on the side in which the abutment areas CA are formed may be formed slightly larger in the vicinity of the up-down parting parts LHL and LHU and the inside-outside parting parts LVI and LVO so that the surfaces of the molded artificial teeth 1 and 2 on the center side of the parting lines PL1 and PL2 protrude 0.01 to 1.00 mm, preferably 0.05 to 0.50 mm, more preferably 0.07 to 0.35 mm more than the surfaces on the outer side. By scaling the surfaces of the artificial teeth 1 and 2 for eliminating this unevenness, shapes after the burr removal are not largely different from designed shapes.

The artificial teeth 1 and 2 according to the present invention are preferably formed by injection molding. Since the burrs are small in the injection molding, the abutment areas CA can be more enlarged, so that the artificial teeth 1 and 2 can be more easily arranged.

Figure 4:
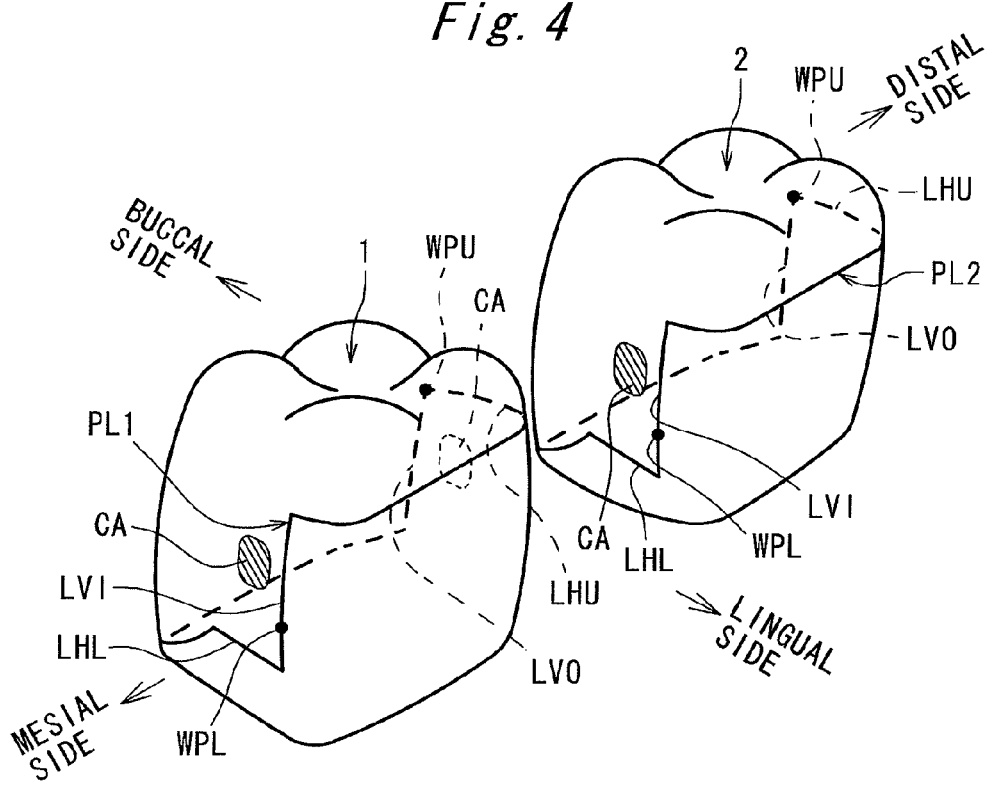
FIG. 4 is a perspective view of a set of artificial teeth according to a second embodiment of the present invention.

Now, FIG. 4 shows a set of artificial teeth according to a second embodiment of the present invention. It should be noted that in description of the present embodiment, the same constituent elements as the first embodiment will be given the same reference numerals, and description thereof will not be repeated.

In the present embodiment, the artificial teeth 1 and 2 respectively have the highest contours WPL on the bottom surface side and the lingual side relative to the abutment areas CA of the mesial surfaces, and the highest contours WPU on the occlusal surface side and the buccal side relative to the abutment areas CA of the distal surfaces.

Since the parting lines PL1 and PL2 of the artificial teeth 1 and 2 respectively pass through the highest contours WPU and WPL, the up-down parting parts LHL on the bottom surface side and the inside-outside parting parts LVI on the lingual side are provided on the mesial surfaces, and the up-down parting parts LHU on the occlusal surface side and the inside-outside parting parts LVO on the buccal side are provided on the distal surfaces.

Figure 5:
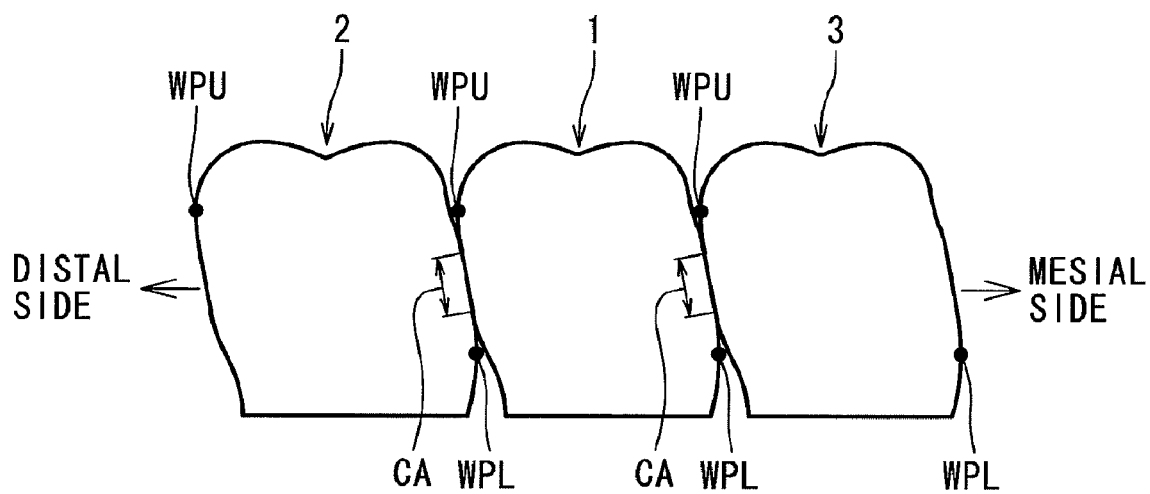
FIG. 5 is a front view of the artificial teeth in FIG. 4 seen from the buccal side.

The set of artificial teeth according to the present embodiment further includes premolar teeth having mesial surfaces and distal surfaces with the same configuration (only a second premolar tooth 3 is shown in FIG. 5). These artificial teeth 1, 2 and 3 have the same direction of the abutment areas CA on the mesial surfaces and the distal surfaces as shown in FIG. 5. Therefore, in the artificial tooth 2, for example, pressing forces respectively received from the adjacent artificial teeth 1 and 3 are balanced at the time of chewing or the like. Thus, the artificial tooth 2 is not pushed in the buccolingual direction by the mastication or not lifted in the occlusal direction.

Contrary to the present embodiment, in the artificial teeth 1, 2 and 3, the highest contours WPU may be formed on the occlusal surface side and the buccal side and the up-down parting parts LHU on the occlusal surface side and the inside-outside parting parts LVO on the buccal side may be provided on the mesial surfaces, while the highest contours WPL may be formed on the bottom surface side and the lingual side and the up-down parting parts LHL on the bottom surface side and the inside-outside parting parts LVI on the lingual side may be provided on the distal surfaces.

At the time of compression molding of such artificial teeth 1, 2 and 3, materials of the hard coats tend to be disproportionately placed distant from the parting lines PL1 and PL2 in the compression direction of the molds (placed further in the molds). Thus, in a case where the hard coats of the artificial teeth 1, 2 and 3 have different thickness, the hard coats of the cusps C which are distant from the inside-outside parting parts LVI on the buccal side in the buccolingual direction among the cusps C on the side in which the up-down parting parts LHL on the bottom surface side are provided in the mesial-distal direction is preferably the thickest.

In the set of artificial teeth according to the present invention, the shapes of the mesial surfaces and the distal surfaces with which principles thereof are already described for the embodiments above are preferably applied to surfaces of all the molar teeth adjacent to each other. Moreover, the present invention can be applied not only to the molar teeth but also to incisors and canines. Therefore, the term "buccal" used for indicating the direction in the description above should also be recognized as "labial" in a case of the incisors and the canines.

Moreover, the present invention is preferably applied not only to the artificial teeth in a mandibular arch but also to a set of artificial teeth which is a pair of teeth in maxillary and mandibular arches. Therefore, the term "lingual" used for indicating the direction in the description above should also be recognized as "palatal" in a case of the teeth in the maxillary arch.

What is claimed is:

1. A set of artificial teeth, comprising:
   a plurality of artificial teeth, wherein
   at least two artificial teeth of the plurality of artificial teeth are adjacent to each other in the mesial-distal direction, a first artificial tooth of the at least two artificial teeth has a first contour position on a first side and a first abutment position on the first side, the first contour position being the highest contour position of the first artificial tooth, a second artificial tooth of the at least two artificial teeth has a second contour position on a second side and a second abutment position on the second side, the second contour position being the highest contour position of the second artificial tooth, the first side being adjacent the second side, and the first and second contour positions being at different positions from each other,
   the first and second artificial teeth are abutted with each other at the first and second abutment positions, the first and second abutment positions being different from the first and second contour positions, and the first abutment position and the second abutment position being flush with a wall of the first artificial tooth and a wall of the second artificial tooth, respectively, each of the plurality of artificial teeth includes a hard coat which covers at least a buccal surface and an occlusal surface of base material, and the base material is covered with the hard coat at one of the first and second abutment positions, and the base material is exposed at the other of the first and second abutment positions.

2. The set of artificial teeth according to claim 1, wherein each of the first and second artificial teeth has a parting line which corresponds to a division position of a mold for forming a respective artificial tooth, and which includes an up-down parting part substantially orthogonal to the occlusal direction, and an inside-outside parting part substantially orthogonal to the buccolingual direction, and each parting line passes through the highest contour position of the respective artificial tooth.

3. The set of artificial teeth according to claim 1, wherein the first contour position is positioned on the occlusal surface side and on the buccal surface side relative to the second contour position.

4. The set of artificial teeth according to claim 1, wherein the first and second abutment positions are disposed between the first and second contour positions in the occlusal direction and the buccolingual direction.

5. The set of artificial teeth according to claim 1, wherein the first and second artificial teeth are in surface contact with each other.

6. The set of artificial teeth according to claim 1, wherein the first and second artificial teeth are molar teeth.

7. The set of artificial teeth according to claim 1, wherein the base material is colored with a different tone from the hard coat.

8. The set of artificial teeth according to claim 2, wherein for each of the first and second artificial teeth, each parting line has the up-down parting part and the inside-outside parting part on a mesial side and a distal side, respectively, the up-down parting part on the mesial side and the up-down parting part on the distal side are located at different positions in an occlusal direction, and the inside-outside parting parts on the mesial side and the inside-outside parting parts on the distal side are located at different positions in a buccolingual direction.

\* \* \* \* \*